US006165798A

United States Patent [19]
Brooks

[11] Patent Number: 6,165,798
[45] Date of Patent: *Dec. 26, 2000

[54] OPTICAL QUANTIFICATION OF ANALYTES IN MEMBRANES

[75] Inventor: Donald Elliott Brooks, Vancouver, Canada

[73] Assignee: University of British Columbia, Vancouver, Canada

[*] Notice: This patent issued on a continued prosecution application filed under 37 CFR 1.53(d), and is subject to the twenty year patent term provisions of 35 U.S.C. 154(a)(2).

[21] Appl. No.: 08/727,998

[22] Filed: Oct. 10, 1996

[51] Int. Cl.[7] .................................................. G01N 1/28
[52] U.S. Cl. ...................... 436/169; 436/172; 436/175; 436/530; 436/533
[58] Field of Search ..................................... 436/164, 169, 436/172, 175, 183, 178, 530, 533

[56] References Cited

U.S. PATENT DOCUMENTS

| | | |
|---|---|---|
| 3,604,929 | 9/1971 | Goulin . |
| 3,899,610 | 8/1975 | Henry . |
| 4,001,139 | 1/1977 | Long . |
| 4,401,765 | 8/1983 | Craig et al. ............................. 436/533 |
| 4,521,522 | 6/1985 | Lundström et al. .................... 436/525 |
| 4,690,907 | 9/1987 | Hibino et al. ........................... 436/514 |
| 4,703,017 | 10/1987 | Campbell et al. ...................... 436/501 |
| 4,703,018 | 10/1987 | Craig et al. ............................. 436/518 |
| 4,855,240 | 8/1989 | Rosenstein et al. .................... 436/514 |
| 4,868,131 | 9/1989 | Hiratsuka ............................... 436/528 |
| 4,975,366 | 12/1990 | Sudo et al. ................................. 435/7 |
| 5,012,681 | 5/1991 | Lentzen . |
| 5,019,496 | 5/1991 | Oster et al. ................................ 435/6 |
| 5,030,558 | 7/1991 | Litman et al. .......................... 435/7.91 |
| 5,039,607 | 8/1991 | Skold et al. ............................. 435/7.5 |
| 5,096,837 | 3/1992 | Fan et al. ................................ 436/514 |
| 5,156,952 | 10/1992 | Litman et al. .......................... 435/7.91 |
| 5,164,294 | 11/1992 | Skold et al. ............................. 435/7.5 |
| 5,187,083 | 2/1993 | Mullis ....................................... 435/91 |
| 5,232,835 | 8/1993 | Litman et al. .......................... 435/7.93 |
| 5,238,652 | 8/1993 | Sun et al. ................................. 422/61 |
| 5,248,619 | 9/1993 | Skold et al. ............................. 436/514 |
| 5,252,696 | 10/1993 | Laas et al. ................................. 528/49 |
| 5,266,497 | 11/1993 | Imai et al. .............................. 436/514 |
| 5,334,513 | 8/1994 | Skold et al. ........................... 435/7.92 |
| 5,401,667 | 3/1995 | Koike ..................................... 436/514 |
| 5,434,051 | 7/1995 | Allard et al. ............................. 435/7.4 |
| 5,451,507 | 9/1995 | Skold et al. ........................... 435/7.92 |
| 5,468,647 | 11/1995 | Skold et al. ............................ 436/514 |

FOREIGN PATENT DOCUMENTS

| | | |
|---|---|---|
| 2059394 | 7/1992 | Canada . |
| 0 271 204 A2 | 6/1988 | European Pat. Off. . |
| 0 274 198 B1 | 7/1988 | European Pat. Off. . |
| 0 284 232 B1 | 9/1988 | European Pat. Off. . |
| 0 447 154 A2 | 9/1991 | European Pat. Off. . |
| 0 451 686 A3 | 10/1991 | European Pat. Off. . |
| 3630999 | 3/1988 | Germany . |
| 61-258172 | 12/1986 | Japan . |
| 62-200244 | 3/1987 | Japan . |
| 63-008561 | 2/1988 | Japan . |
| 2 204 398 | 11/1988 | United Kingdom . |
| WO 85/05687 | 12/1985 | WIPO . |
| WO 87/07386 | 12/1987 | WIPO . |
| WO 88/01744 | 3/1988 | WIPO . |
| WO 91/18276 | 11/1991 | WIPO . |
| WO 93/04357 | 3/1993 | WIPO . |
| WO 93/18067 | 9/1993 | WIPO . |
| WO 93/25910 | 12/1993 | WIPO . |
| WO 94/00751 | 1/1994 | WIPO . |
| WO 94/15193 | 7/1994 | WIPO . |
| WO 95/06240 | 3/1995 | WIPO . |

OTHER PUBLICATIONS

Database CAPLUS, Abstract No. 1987:72555, Kasahara et al., Anal. Chem., 59(5), 787–9, 1987.

Webster's Ninth New Collegiate Dictionary, Merriam–Webster Inc. p. 1254, 1987.

Hierholzer, J.C. et al., "Spectrophotometric Quantitation of Peroxidase–Stained Protein Bands Following Gel Electrophoresis and the Western Blot Transfer Technique with Respiratory Syncytial Virus," *Jour. of Virological Methods* 8:265–268 (1984).

Vachereau, A., "Transparency of nitrocellulose membranes with Triton X–114," *Electrophoresis* 10:524–527 (1989).

Klimov, A.D. et al. "Improved Immunochromatographic Format for Competitive–Type Assays," *Clinical Chemistry* 41(9):1360 (1995).

Laitinen, M.P.A. and Vuento, M., "Immunochromatographic Assay for Quantification of Milk Progesterone", *Acta Chemica Scandinavica*, 50:141–145 (1996).

Roberts, M.A. and Durst, R.A., "Investigation of Liposome–Based Immunomigration Sensors for the Detection of Polychlorinated Biphenyls", *Anal. Chem.*, 67:482–491 (1995).

Borque, L., et al., "Automated Quantitative Nephelometric Latex Immunoassay for Determining Ferritin in Human Serum", *Journal of Clinical Laboratory Analysis*, 6:239–244 (1992).

Birnbaum, S., et al., "Latex–Based Thin–Layer Immunoaffinity chromatography for Quantitation of Protein Analytes", *Analytical Biochemistry*, 206:168–171 (1992).

Siebert, S.T.A., et al., "Liposome immunomigration field assay device for Alachlor determination", *Analytica Chimica Acta*, 282:297–305 (1993).

Siebert, S.T.A., et al., "Improved liposome immunomigration strip assay for alachlor determination", *Analytica Chimica Acta*, 311:309–318 (1995).

Reeves, S.G. and Durst, R.A., "Novel Optical Measurement Approach for the Quantitation of Liposome Immunomigration Assays", *Analytical Letters*, 28:23347–2362 (1995).

von Olleschik–Elbheim, L., et al., "Quantification of immunological membrane reactions employing a digital desk top scanner and standard graphics software", *Jour. of Immun. Methods*, 197:181–186, (1996).

*Primary Examiner*—Jan Ludlow
*Attorney, Agent, or Firm*—Hamilton, Brook, Smith & Reynolds, P.C.

[57] ABSTRACT

Methods for measuring the amount of an analyte in a membrane, by applying to the membrane a clearing agent, are disclosed. The clearing agent can be an agent that has approximately the same refractive index as the membrane; alternatively, the clearing agent can be a dissolving agent, that dissolves the membrane. The analyte can be labelled to facilitate detection. Representative labels include fluorescent labels and detectable particles.

10 Claims, 1 Drawing Sheet

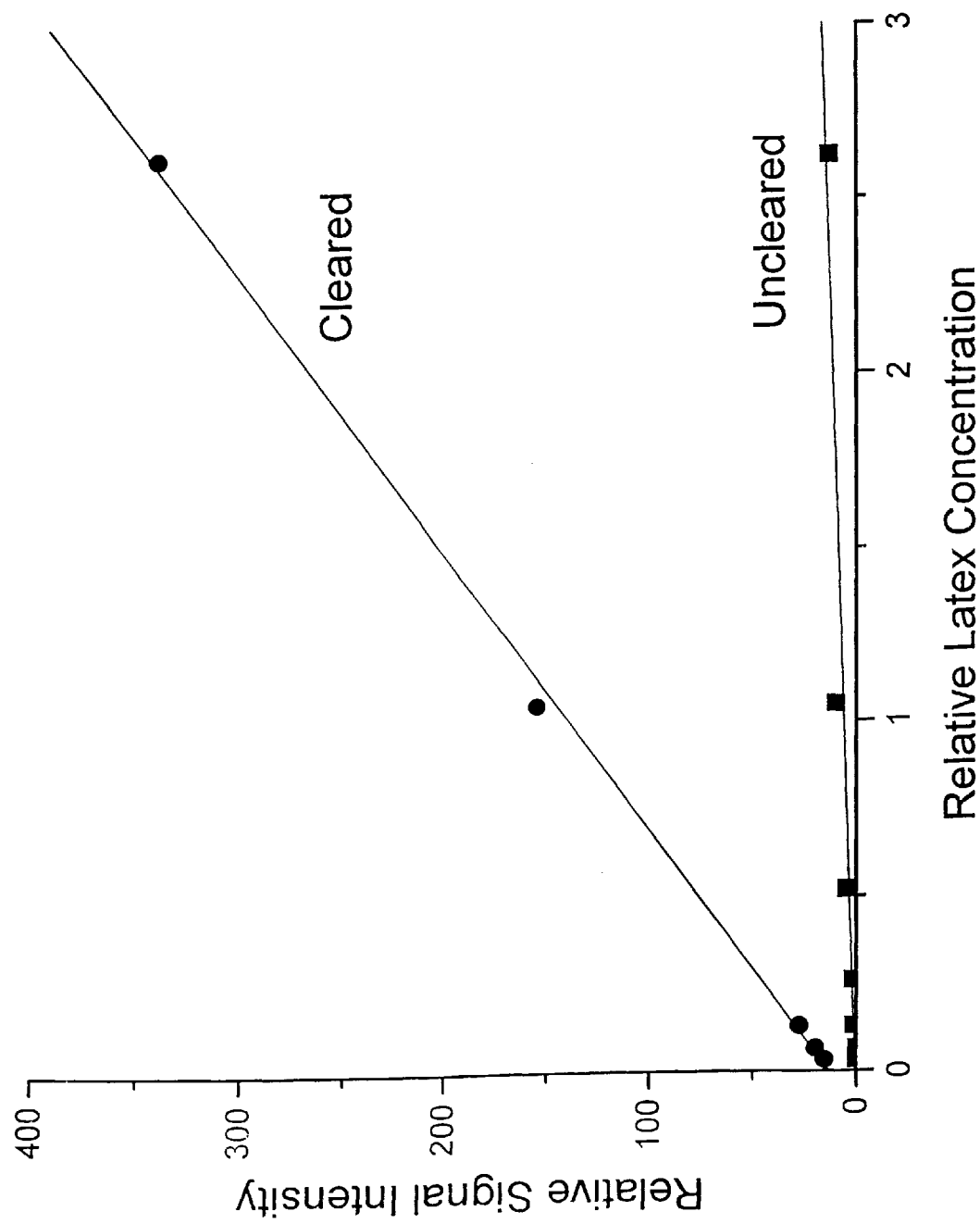

OPTICAL QUANTIFICATION OF ANALYTES IN MEMBRANES

BACKGROUND OF THE INVENTION

Quantitative analysis of cells and analytes in fluid samples, particularly bodily fluid samples, often provides critical diagnostic and treatment information for physicians and patients. Immunological testing methods (Kennedy, D. M. and S. J. Challacombe, eds., *ELISA and Other Solid Phase Immunoassays: Theoretical and Practical Aspects*, John Wiley and Sons, Chichester (1988)), which take advantage of the high specificity of the antigen-antibody reaction, provide one approach to measurement of analytes. Immunoassays which provide a quantitative measurement of the amount of an analyte in a sample often use complex, multistep procedures and expensive analyzers available only in a laboratory setting. Immunochromatographic assays, such as those described in GB 2,204,398A; U.S. Pat. Nos. 5,096,837, 5,238,652, and 5,266,497; Birnbaum, S. et al., *Analytical Biochem.* 206:168–171 (1992); Roberts, M. A. and R. A. Durst, Analytical Chem. 67:482–491 (1995); and Klimov, A. D. et al., *Clinical Chem.* 41:1360 (1995), are simpler. Immunochromatographic assays rely for their interpretation on the observation of colored reaction products, usually colored particles, in a particular region of a membrane. To obtain a quantitative measure of the amount of an analyte detected in an immunochromatographic assay, the amount of colored particles is analyzed.

Measurement by optical means of the amount of particles accumulated in one or more regions of a membrane is usually performed by reflectometry or densitometry. In these techniques, a light beam is either reflected or transmitted through the colored portion of the membrane, and the light intensity reaching a detector is measured. Other methods include obtaining, with a video camera, the image of the membrane illuminated with transmitted or reflected light, and performing image analysis on a frame of the video record. Although image analysis software allows considerable manipulation of the image to optimize sensitivity in detection of the particles, these methods suffer from light scattering by the membrane fibers in which the particles are imbedded. The multiple scattering that results obscures the optical signal produced by the particles and dramatically increases the noise level in the measurement.

SUMMARY OF THE INVENTION

The current invention pertains to methods for quantifying the amount of an analyte in a membrane, in which the membrane is rendered transparent by a clearing agent, and the amount of analyte is measured using an optical means. The membrane can be rendered transparent by wetting the membrane with a clearing agent that has a refractive index ($n_D$) that is approximately equal to the refractive index of the substance from which the membrane is made. For example, a nitrocellulose membrane can be cleared with polyvinylpyrrolidone, polyethleneimine, or benzyl alcohol. Alternatively, the membrane is rendered transparent by applying to the membrane a dissolving agent that dissolves the membrane to form a clear background. For example, a nitrocellulose membrane can be cleared using polyethylene glycol as a dissolving agent. The amount of analyte in the membrane is measured using an optical sensor, such as a sensor that measures fluorescence or light scattering. The analyte can be labelled with a fluorescent label or with detectable particles, such as inorganic particles, organic molecules, liposomes, or organic polymer latex particles, in order to facilitate quantification of the analyte.

Rendering the membrane transparent facilitates detection of the analyte and enhances accuracy and sensitivity of the quantification of the particles, by eliminating or minimizing light scattering by the membrane fibers, and thereby decreasing the noise level caused by background interference in the measurement. The methods are simple, rapid, and can be used for a wide variety of analytes and membranes.

BRIEF DESCRIPTION OF THE FIGURE

The FIGURE is a graphic representation of the relative signal intensity for various concentrations of latex particles in cleared and in uncleared nitrocellulose membranes.

DETAILED DESCRIPTION OF THE INVENTION

The current invention pertains to methods of optically detecting and quantifying analytes in a membrane. As described herein, the accuracy and sensitivity of quantification of analyte in a membrane with a light scattering or fluorescence means is enhanced by rendering the membrane transparent. The term, "analyte," as used herein, refers to the molecule, compound, particle, cell fragment, cell, or biological entity for which the amount will be quantified. Examples of analytes include proteins, such as hormones or enzymes; glycoproteins; peptides; small molecules; polysaccharides; antibodies; nucleic acids; drugs, including drugs of abuse; toxins; inorganic particles such as colloidal gold particles; viruses or virus particles; bacteria; whole cells; portions of bacteria or cells; and other compounds. More than one analyte can be quantified. Also or in addition, a control analyte can be quantified.

To perform the methods of the invention, a membrane of interest is provided, having therein the analyte to be quantified (if any is present). The membrane is made of a substance having the capability to be rendered transparent. The membrane can be translucent (i.e., is capable of allowing diffuse light to pass through), or opaque (i.e., incapable of allowing light to pass through). Examples of membrane substances include: cellulose, cellulose nitrate, cellulose acetate, glass fiber, nylon, polyelectrolyte ion exchange membrane, acrylic copolymer/nylon, and polyethersulfone. In a preferred embodiment, the membrane is made of cellulose nitrate, cellulose acetate, glass fiber, or nylon. The membrane can consist of more than one substance: for example, it may consist of nitrocellulose with a Mylar™ backing. If the membrane is made of more than one substance, each substance should either be transparent, or be capable of being rendered transparent.

Analyte "in" or "held in" the membrane includes analyte present on the surface of the membrane, as well as analyte within the substance of the membrane. The analyte can be held in the membrane by adhering to the membrane (e.g., to membrane fibers). Alternatively, the analyte can be trapped within pores or interstices of the membrane. The analyte can also be held in the membrane by applying the analyte in a fluid to the membrane, and then allowing the membrane to dry.

In another embodiment, the analyte is held in the membrane by binding of the analyte to an analyte-binding agent which is immobilized in the membrane. An analyte is "bound" to an analyte-binding agent if it is physically or chemically attached to, adhered to, or associated with, the analyte-binding agent. Analyte-binding agents include antibodies specific for the analyte, receptors that specifically bind to the analyte, genetically engineered binding reagents, bacterial or viral adhesions, aptimers, chelators, binding reagents generated by combinatorial chemistry, or other molecules that bind to the analyte. For example, the analyte can be bound to the membrane by interaction of the analyte with an antibody that is immobilized in the membrane. The term, "antibody," as used herein, encompasses both polyclonal and monoclonal antibodies, as well as mixtures of more than one antibody reactive with an epitope of interest (e.g., a cocktail of different types of monoclonal antibodies reactive with the peptide). The term antibody is further intended to encompass whole antibodies and/or biologically functional fragments thereof, chimeric antibodies comprising portions from more than one species, humanized antibodies, human-like antibodies, surfaced antibodies, and bifunctional antibodies. Biologically functional antibody fragments which can be used are those fragments sufficient for binding of the antibody fragment to the analyte of interest.

The analyte can be labelled to facilitate detection. Examples of such labels include luminescent labels; phosphorescent labels; colorimetric labels, such as dyes; or fluorescent labels. Representative fluorescent labels include fluorescein, fluorescein isothiocyanate (FITC), rhodamine, tetramethyl rhodamine isothiocyaniate (TRITC), Texas red, phycoerythrin, or other fluorochromes. The analyte can be directly labelled, such as by attachment of a fluorochrome to the analyte. Alternatively, the analyte can be indirectly labelled, such as by labelling of the analyte with a reporter molecule (e.g., biotin, digoxigenin), which can be recognized by a reporter-binding molecule (e.g., avidin, streptavidin, or digoxigenin antibody). The reporter-binding molecule is in turn attached to a fluorescent label. The analyte can also be labelled with an antibody that specifically binds to the analyte. The analyte-binding antibody can be conjugated to a fluorochrome. Alternatively, it can be labelled through the use of a secondary antibody conjugated to a fluorochrome, where the secondary antibody recognizes and is specific for the primary, analyte-binding antibody; or through the use of streptavidin-biotin. conjugates, where the primary, analyte-binding antibody is recognized by a biotinylated secondary antibody, which interacts with a streptavidin fluorochrome.

In another embodiment, the analyte can be labelled with a detectable particle. A "detectable particle," as used herein, is a particle which can be detected using an optical sensor.

An "optical sensor" is a sensor that detects electromagnetic radiation method based on the measurement or estimation of a characteristic of light, such as light intensity, reflection, refraction, polarization, fluorescence lifetime, or light of a particular wavelength. Examples are fluorescence intensity measurements, light scattering intensity measurements, analysis of images from optical or fluorescence microscopy, densitometry, and reflectometry.

The analyte is bound to the detectable particle in an appropriate manner, such as by binding of the analyte to an analyte-specific antibody coated on the surface of the particle. Examples of detectable particles include colloidal gold particles; colloidal sulphur particles; colloidal selenium particles; colloidal barium sulfate particles; colloidal iron sulfate particles; metal iodate particles; silver halide particles; silica particles; colloidal metal (hydrous) oxide particles; colloidal metal sulfide particles; colloidal lead selenide particles; colloidal cadmium selenide particles; colloidal metal phosphate particles; colloidal metal ferrite particles; any of the above-mentioned colloidal particles coated with organic or inorganic layers; protein or peptide molecules; liposomes; or organic polymer latex particles. In a preferred embodiment, the particles are polystyrene latex beads, and particularly, polystyrene latex beads that have been prepared in the absence of surfactant, such as surfactant-free Superactive uniform Aldehyde/Sulfate Latexes (Interfacial Dynamics Corp., Portland, Oreg.). Detectable particles can be additionally labelled to enhance detection: for example, a liposome or a latex bead can be dyed or can be made to incorporate fluorochromes.

The type of label for the analyte will vary, depending on the analyte, the membrane, method of detection used, the results sought, and other factors. If the particles themselves are not transparent (i.e., if the particles can be detected using an optical sensor), it may not be necessary to label the particles.

To conduct the assays of the invention, a clearing agent is used. The clearing agent is an agent that causes the membrane to become transparent; that does not dissolve the analyte or interfere with any label used; and that does not significantly displace the analyte. The term, "transparent," as used herein, indicates that light passes through the membrane with little or no scattering caused by the substance of the membrane.

In one embodiment, the clearing agent is within the membrane itself. For example, the clearing agent can be a solid substance that is incorporated into the membrane. For example, if the membrane is nitrocellulose, the clearing agent can be polyethylene glycol, preferably polyethylene glycol having a molecular weight of 1,000. The clearing agent is activated at an appropriate time using an appropriate means for activation. For example, if the clearing agent is a solid agent that liquifies at a certain temperature, and that clears the membrane when it is liquified, the clearing agent can be activated by heating the membrane containing the clearing agent to an appropriate temperature. When the clearing agent liquifies, it clears the membrane.

In another embodiment, the clearing agent is applied onto the membrane to be assayed for the quantity of analyte. The clearing agent is applied to the membrane using standard techniques known to those of ordinary skill in the art. For example, clearing agent can be coated, sprayed, dropped, wicked, sprinkled, or blotted into the membrane. Alternatively, the membrane can be briefly immersed in the clearing agent. In a preferred embodiment, the clearing agent is a liquid, because of the ease of application of a liquid to the membrane.

In one embodiment, the clearing agent is an agent that, when it is a liquid, has approximately the same refractive index as the membrane. The intensity of scattered light depends on the square of the difference in refractive index between the scattering object and the medium in which it is immersed. Therefore, an agent having approximately the same refractive index as the membrane will eliminate interference. For example, the refractive index of nitrocellulose is $n_D$=1.538 (the subscript refers to the sodium D line, the wavelength of which is 589 nm, which is a common wavelength at which to measure the refractive index). Therefore, a clearing agent for nitrocellulose has a refractive index between approximately 1.530–1.545, and preferably between approximately 1.535–1.540, and more preferably approximately 1.538. Representative clearing agents for nitrocellulose include polyvinylpyrrolidone ($n_D$=1.51–1.54, depending on molecular weight); polyethyleneimine (PEI; $n_D$=1.52–1.53, depending on molecular weight) and benzyl alcohol ($n_D$=1.538). In a preferred embodiment, PEI having a molecular weight of approximately 700 is used as a clearing agent for a nitrocellulose membrane. Other clearing agents include mixtures of water and PEI for glass fiber membranes, the exact composition determined to be that which matches the index of refraction of the glass ($n_D$= 1.46–1.52, depending on type). If the clearing agent is an agent that has approximately the same refractive index as the membrane, and if the means for detection of the analyte is light scattering, then any label used for the analyte should have a refractive index that is different from that of the clearing agent and the membrane. If a different label is used (such as fluorescence), than it is not necessary for the clearing agent to have a refractive index different from that of the label.

In a second embodiment of the invention, the clearing agent is a dissolving agent. A "dissolving agent," as described herein, is an agent that dissolves the membrane into a clear substance. The dissolving agent is viscous enough to dissolve the membrane, without significantly displacing the analyte from the position it held prior to application or activation of the dissolving agent. For example, nitrocellulose is dissolved by low molecular weight polymers such as polyethylene glycols (PEGs). A single polymer, or a mixture of different polymers, can be used as the clearing agent.

The membrane is maintained under conditions sufficient to allow clearing of the membrane. The term, "clearing" of the membrane, indicates that the membrane becomes transparent. Clearing of the membrane, as described herein, also refers to dissolving the membrane to a clear (transparent) substance.

For example, if the clearing agent is an agent within the membrane or applied to the membrane that, when liquefied, clears the membrane, the membrane is maintained at an appropriate temperature to liquefy the clearing agent. In another example, enough time should be allowed to elapse to allow clearing to proceed. The clearing time varies from seconds to hours, depending on the viscosity of the agent and the membrane characteristics. Some agents act effectively instantaneously upon application or activation; others require time to clear the membrane.

Following clearing of the membrane, the amount of the analyte can be quantified by an appropriate sensor that detects electromagnetic radiation, such as an optical sensor. For example, if the analyte is labelled with a fluorescent label, the amount of analyte can be quantified by measuring fluorescence intensity. The quantity of analyte can be calculated based on the strength of the fluorescence signal. Alternatively, if the analyte is detectable without a label, or if the analyte is labelled using a detectable particle, the amount of analyte can be quantified by measuring the light scattering at one or more angles from the incident light direction A representative optical sensor, which could be used for a wide range of different types of membranes and analytes, could include the following: a filter or other means to select an emission wavelength for fluorescence measurements; a single or multichannel photodetector device to measure light intensity; a light source for excitation of fluorescence or measurement of reflectance; a collimated light source for forward light scattering measurement; and/or a diffuse light source for transmittance measurement of concentrated analyte. The light source and/or the filter could be selected for the appropriate mode of measurement desired.

More than one type of analyte can be quantified at the same time: for example, analytes having different fluorescent labels can be detected by measuring the fluorescent intensity of each label. Alternatively, one analyte can be quantified by fluorescence, and another by measuring light scattering. A control analyte can also be used and quantified.

The methods of the invention permit highly sensitive detection and quantification of analyte in a membrane. The methods are particularly useful for quantitative immunochromatographic assays to assess the quantity of analytes in a fluid sample, using a Rapid Antigen Measurement Platform (RAMP™) apparatus. In such a quantitative immunochromatographic assay, a RAMP™ apparatus is used. In one embodiment, the apparatus includes a membrane strip made of cellulose nitrate; the membrane strip has an application point, a detection zone, and a contact region between the application point and the detection zone. Imbedded in the contact region is a population of particles, such as colloidal metal particles, organic molecules, liposomes, or organic polymer latex particles, coated with an antibody to the analyte of interest. A detection reagent, such as antibody to the analyte of interest, or the analyte of interest itself, is immobilized in the detection zone. A fluid sample to be assayed for the analyte of interest is applied to the application point, and the apparatus is maintained under conditions which allow capillary action of fluid to transport analyte of interest through the membrane strip to the contact region, so that when analyte reaches the contact region, it binds to the antibody-coated particles. The antibody-coated particles are mobilized by the fluid and move by capillary action through the membrane to the detection zone. In the detection zone, the detection reagent interacts with the antibody-coated particles, leading to arrest of analyte-bound antibody-coated particles in the detection zone. The amount of analyte-bound antibody-coated particles in the detection zone is quantified. The amount of analyte in the fluid sample can be calculated, based on amount of analyte-bound antibody-coated particles in the detection zone. More detailed teachings concerning quantitative immunochromatographic assays are described in U.S. patent application Ser. No. 08/625,048, entitled "Quantitative Immunochromatographic Assay", filed on Mar. 29, 1996, now U.S. Pat. No. 5,753,517 the entire teachings of which are incorporated herein by reference. The accuracy and sensitivity of this quantitative immunochromatographic assay is greatly enhanced by the methods described herein. After arrest of analyte-bound antibody-coated particles in the detection zone of the membrane, the clearing agent is applied to the RAMP™ apparatus membrane, and apparatus is maintained under conditions sufficient to allow clearing of the membrane. Quantification of the analyte-bound antibody-coated particles in the detection zone is enhanced approximately 20-fold by clearing of the membrane.

The invention is further illustrated by the following Example.

EXAMPLE

Quantitative Analysis of Latex Particles Imbedded in a Nitrocellulose Membrane

A video image analysis system utilizing a DVC 10 bit digital CCD camera mounted on a Wild APOZOOM lens system, an Imaging Technology IC-PCI-2.0 frame grapper and OPTIMAS 5.2 image analysis software on a 120 MHZ Pentium PC was used to quantitate the signal produced by a population of latex particles imbedded in a Sartorius NC 5 nitrocellulose membrane having a transparent Mylar™ backing. Samples of latex particles, stained navy blue and having a diameter of 0.53 µm, were coated with bovine serum albumin (BSA) to a surface concentration of approximately $3 \times 10^{-4}$ mg/cm$^2$ and allowed to travel approximately three cm by capillary action in 0.05 M tris-HCl buffer to a detection zone of the nitrocellulose membrane. The detection zone (the area of the membrane which was analyzed to quantify the analyte) had been prepared by applying 3×5 µl of a polyclonal antibody preparation of rabbit anti-BSA IgG to the membrane, blocking with it polyvinyl alcohol (MW 15,000) for approximately four hours, then washing three times with distilled water. The latex concentration was varied from $1.6 \times 10^{-5}$ g/ml to $1.3 \times 10^{-3}$ g/ml, and 5 µl of latex suspension was applied to the membrane at the opposite end from the detection zone. No latex was detected beyond the detection zone in any membrane upon completion of migration in the membrane, thus implying that essentially all of the latex had been arrested in the detection zone. Duplicate membrane strips, each pair having a different concentration of latex particles, were prepared.

One of each set was imaged with transmitted light without the use of a clearing agent, while the second was treated with a drop of PEG 600 over the detection zone before analysis. For the untreated membranes, the analysis was performed with the video camera on the vertical axis above the membrane and the light supplied by a diffuse source below the membrane and aimed directly at the camera. The focussed image of the detection zone produced by the transmitted light was then analyzed.

For the membranes treated with a clearing agent, the analysis was performed by recording and analyzing the image obtained when the membrane was illuminated from below with a collimated beam oriented at an angle of about 30 degrees from the vertical, with the camera again located above the sample on the vertical axis. In this case the background in the focussed image of the detection zone appeared dark, with the arrested latex forming a bright band as a result of the forward scattered light collected by the camera.

In each case, the image was optimized by background subtraction, and the final image was integrated to provide the integrated pixel intensity representing the signal from the latex particles.

Results are shown in the FIGURE, where the relative integrated signal intensity is plotted as a function of the relative number of latex particles applied to each membrane. The results demonstrate a large increase in signal provided by the cleared membrane relative to the uncleared membrane.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

What is claimed is:

1. A method of measuring the amount of an analyte of interest in a membrane, comprising the steps of:
    a. applying to the membrane a clearing agent that is a dissolving agent selected from the group consisting of: a low molecular weight polymer and a mixture of low molecular weight polymers, wherein the clearing agent is an agent that causes the membrane to become transparent, such that light passes through the membrane with little or no scattering caused by the substance of the membrane; that does not dissolve the analyte or interfere with any label; and that does not significantly displace the analyte from its position on the membrane;
    b. maintaining the membrane under conditions sufficient to allow clearing of the membrane; and
    c. measuring the amount of the analyte using an optical sensor.

2. The method of claim 1, wherein the membrane is nitrocellulose.

3. The method of claim 2, wherein the dissolving agent is a polyethylene glycol.

4. The method of claim 1, wherein the analyte is labelled.

5. The method of claim 4, wherein the label is a fluorescent label.

6. The method of claim 5, wherein the optical sensor measures intensity of fluorescence.

7. The method of claim 4, wherein the label is a detectable particle.

8. The method of claim 7, wherein the detectable particle is fluorescently labeled.

9. The method of claim 7, wherein the particle is a latex bead.

10. The method of claim 7, wherein the optical sensor measures intensity of scattered light.

* * * * *